United States Patent [19]

Tacklind et al.

[11] Patent Number: 5,704,366
[45] Date of Patent: Jan. 6, 1998

[54] SYSTEM FOR MONITORING AND REPORTING MEDICAL MEASUREMENTS

[75] Inventors: Christopher A. Tacklind, Palo Alto; Matthew H. Sanders, Los Altos Hills; Geoffrey B. Walne, Atherton, all of Calif.

[73] Assignee: Enact Health Management Systems, Mountain View, Calif.

[21] Appl. No.: 247,727

[22] Filed: May 23, 1994

[51] Int. Cl.⁶ ..................... A61B 5/08
[52] U.S. Cl. ............ 128/716; 128/725; 128/726; 128/671; 128/904
[58] Field of Search .............. 128/671, 716, 128/725, 726, 728, 903, 904

[56] References Cited

U.S. PATENT DOCUMENTS

| | | |
|---|---|---|
| 3,572,316 | 3/1971 | Vogelman et al. ............ 128/671 |
| 3,645,133 | 2/1972 | Simeth et al. . |
| 3,797,479 | 3/1974 | Graham . |
| 3,818,901 | 6/1974 | Sanctuary et al. . |
| 3,960,142 | 6/1976 | Elliott et al. . |
| 4,034,743 | 7/1977 | Greenwood et al. . |
| 4,053,951 | 10/1977 | Hudspeth et al. ............ 128/671 |
| 4,241,739 | 12/1980 | Elson . |
| 4,267,845 | 5/1981 | Robertson, Jr. et al. ............ 128/725 |
| 4,282,883 | 8/1981 | Yerushalmy ............ 128/726 |
| 4,296,756 | 10/1981 | Dunnine et al. ............ 128/725 |
| 4,444,201 | 4/1984 | Itoh . |
| 4,495,944 | 1/1985 | Brisson et al. . |
| 4,679,566 | 7/1987 | Tamm ............ 128/671 |
| 4,972,842 | 11/1990 | Korten et al. ............ 128/716 |
| 5,020,516 | 6/1991 | Biondi et al. ............ 128/671 |
| 5,137,026 | 8/1992 | Waterson et al. . |
| 5,246,010 | 9/1993 | Gazzara et al. ............ 128/725 |
| 5,307,263 | 4/1994 | Brown ............ 364/413.9 |
| 5,320,107 | 6/1994 | O'Brien ............ 128/725 |
| 5,339,825 | 8/1994 | McNaughton et al. ............ 128/725 |

FOREIGN PATENT DOCUMENTS

| | | |
|---|---|---|
| 0 553 372 A1 | 8/1993 | European Pat. Off. ...... A61B 5/0205 |
| 2224567 | 5/1990 | United Kingdom . |
| WO89/00024 | 1/1989 | WIPO ............ A61B 5/00 |

Primary Examiner—Angela D. Sykes
Assistant Examiner—Stephen Huane
Attorney, Agent, or Firm—Townsend and Townsend and Crew LLP

[57] ABSTRACT

A system for monitoring and reporting medical information includes a stand-alone monitor for storing data records comprising measured values and time stamps and for transmitting the records to a remote reporting unit over a communication system. The remote reporting unit includes a relational data base that is updated when records are downloaded from the monitor; a report generator for generating chronological graphs of the measured values for a particular patient; and a report transmitting unit for transmitting reports to a requesting health care provider.

5 Claims, 14 Drawing Sheets

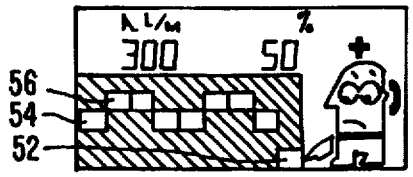

SAMPLE SCREENS
NUMBERS CORRESPOND TO THE BLINKING SQUARE.
TEST RESULT: PEF=300 LITERS/MINUTE
%PB= 50% -- RED ZONE
CROSS AND TELEPHONE SYMBOL ARE REMINDERS TO SEEK MEDICAL ATTENTION.

*FIG. 4A.*

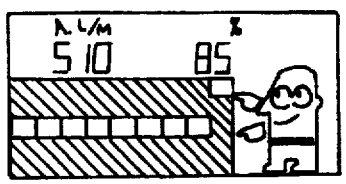

TEST RESULT: PEF=510 LITERS/MINUTE
%PB=85% -- GREEN ZONE
ZONE BOUNDARY CROSSED SO WELBY'S HAND JUMPS FROM YELLOW TO GREEN ZONE.

*FIG. 4B.*

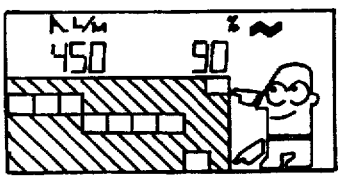

TEST RESULT: PEF=450 LITERS/MINUTE
%PB=90% -- GREEN ZONE
ZONE BOUNDARY CROSSED SO WELBY'S HAND JUMPS FROM RED TO GREEN ZONE. SYMBOL FOR HIGH VARIABILITY IS ON.

*FIG. 4C.*

 High GREEN ZONE:_____to_____

 GREEN ZONE:_____to_____ [90-100%]
☺This stable zone is where you should be every day!

■ Ventolin or Provenul metered dose inhaler or Rotahaler
  ■ 30 min pre-exercise
  ■ Otherwise not needed at this level ■ Intal or Vancerit/Beclovent or Azmacort __puffs twice a day

*FIG. 4D-1.*

High YELLOW ZONE: _____ to _____ [70-90% of best]
→Important! This is not the zone where you should be every day -- Call if you either keep dropping into this zone or can't blow higher than this zone every day.

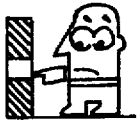

● Restart 1-2 puffs Ventolin or Proventil inhaler with spacer or 1 Ventolin Rotacap every 4 to 6 hours until peak flow goes back to Green Zone level.

■ After taking the above Ventolin or Proventil, continue taking Intal or Vanceril/Beclovent or Azmacort at usual dose twice a day.

Low YELLOW ZONE: _____ to _____ [50-70% of best]
→Call your physician if stuck in this zone (often an indication of a chronic sinus infection) -- Call if you bounce in and out of this very unstable zone two days in a row.

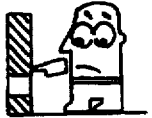

■ Intensify Ventolin or Proventil inhaler to 3 puffs or Ventolin rotacap to 2 capsules (3-5 minutes apart) or one 2.5 mg Ventolin or Proventil nubulizer treatment every 2-4 hours.

■ Intensify Intal or Vanceril/Beclovent or Azmacort by doubling usual dose to __ puffs per day 2 or 3 times a day for 7-14 days.

RED ZONE: below _____ [below 50% of best]
→This is an emergency! Don't wait and see what happens.

■ You will likely need to start oral steroids for a few days. The choices are either in the forms of syrups of Pediapred or Prelone or tablets of prednisone or methylprednisolone at a dose of _____.

■ The dose and frequency of treatments with Ventolin or Proventil is very important and may need to be increased. Every severe asthma attack can be different -- so don't rely on what has worked in the past. There is no substitute for on-the-spot advice. Call!

■ If possible, continue taking intensive doses of Intal or Vanceril/ Beclovent or Azmacort according to your physician's advice.

*FIG. 4D-2.*

NOTE 1: PULSE WIDTH MEASURING CIRCUIT, 2 MICROSECOND RESOLUTION
NOTE 2: PULSE WIDTH MODULATED DIGITAL-TO-ANALOG CONVERTER, 8 BIT RESOLUTION

SYSTEM FOR MONITORING AND REPORTING MEDICAL MEASUREMENTS

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or record, but otherwise reserves all copyright rights whatsoever.

BACKGROUND OF THE INVENTION

Recent developments in medical device technology have led to the development of low cost devices for measuring physiological characteristics of a patient suffering from a chronic disease. As a result of these measurements marked improvements in treatment are possible because the type of treatment is responsive to the result of a measurement.

As an example, diabetes patients now measure blood sugar several times a day to determine when to administer insulin and how much insulin is required. Management of other chronic diseases could require monitoring multiple physiological measurement including pulse rate, blood pressure, respiration rate, body weight, spirometric parameters, etc.

Unfortunately, however, the possibilities of the improved technology often have not been realized because of patient inability to use the device, or understand the meaning of the device output. Often, effective treatment requires that measurements be taken over time and plotted on a graph to determine patient tendencies and the oncoming of a crisis. There are also problems on the health care provider side, with increased physician workload preventing the physician from monitoring compliance and gathering, formatting data, and interpreting data.

The following is a detailed discussion of the problems inherent in treating chronic asthma. Recent events suggest that there is an abundant need for data collection and reporting tools for use in the treatment of chronic asthma. The U.S. National Center for Health Statistics estimates that 12 million Americans—nearly 5% of the population—have asthma. Asthma morbidity and mortality rates increased dramatically during the 1980's. The reasons for these increases are not well understood. In the 1980's leading medical researchers began to view asthma as primarily an inflammatory response in the airways rather than bronchospasm. Consequently, they began advocating a new pharmacological therapy, anti-inflammatory medications. Furthermore, numerous studies of self management programs have documented the importance of early warning detection and patient-physician cooperative management in the long-term treatment of chronic asthma.

In August 1991 the National Asthma Education Program (NAEP), which was organized by the National Institutes of Health, published its Expert Panel Report: "Guidelines for the Diagnosis and Management of Asthma". In its foreword the Expert Panel Report states: "People with asthma can expect to control their symptoms, prevent asthma episodes, be physically active, and breathe normally. This report presents guidelines to help clinicians and patients meet these goals of asthma care." The report suggests regimens for pharmacological therapy, emphasizes the role of anti-inflammatory medication, and warns about the risks of over- and under-medication. The report stresses the importance of fostering a partnership among patient, family, and physician in the achievement of a successful self-management program for asthma sufferers.

Peak Flow Meters and Asthma Management

Peak flow meters have been around for a number of years. Many clinicians recognize that daily PEFR measurements can provide early warnings of an asthma attack. However, self-management programs which urge daily peak flow monitoring continue to be the exception rather than the rule. In advocating a preventative approach to asthma care, the National Asthma Education Program is urging clinicians and patients to adopt a preventative rather than an interventional approach to managing asthma.

The peak flow meter measures Peak Expiratory Flow (PEF), defined as the maximum rate at which an individual can expel air from the lungs, using maximal effort from full inhalation. PEF is measured in liters per minute. The highest value obtained in up to three attempts is recorded into a peak flow diary, which is usually a handwritten chart.

The personal spirometer typically measures several respiratory parameters, including the Forced Expiretory Volume ($FEV_1$), defined as the volume of air expelled by an individual in the first second of exhalation, using maximal effort from full inhalation. $FEV_1$ is measured in liters.

Physicians can gain several advantages by having access to accurate respiratory status data:

in evaluating the efficacy of the current medication regimen in detecting seasonal patterns, a rising or falling personal best, PEF and $FEV_1$ trends in assessing airway stability over large blocks of time in assessing compliance with the self management program, including daily peak flow monitoring in providing a basis for an incentive system that physicians and/or parents can use to reward good compliance According to the Expert Panel Report, PEF and $FEV_1$ are useful in detecting the early signs of airway instability and in evaluating the efficacy of medication regimens. For instance, a patient can take PEF samples before and after administering a bronchodilator and thus have a basis upon which to evaluate the drug's efficacy in treating that patient's acute asthma episodes.

The Expert Panel Report is attempting to steer primary care physicians toward supporting patient self-management programs that entail daily peak flow monitoring. It recommends that patients 5 years or older with moderate or severe asthma measure their peak expiratory flow rates on a daily basis. Furthermore, it recommends that all patients and physicians employ peak flow meters and/or personal spirometers in their self asthma management programs.

The chairman of the NAEP's Expert Panel, Albert L. Sheffer, M.D., expressed his concerns about inadequacies in many home management programs for asthma: "All asthma patients who need daily therapy should be monitored with a peak flow meter. Meters are now used on fewer than 25% of those patients."

Guillermo R. Mendoza, M.D., a renowned expert in asthma diagnosis and treatment, made this statement: "Since 1978, despite a growing consensus about the value of peak flow monitoring, only a minority of primary care providers in the U.S. have adopted peak flow in their office practice. Few high risk asthma patients in this country have peak flow meters at home or know how to use them effectively."

A U.S. government publication makes this recommendation: "Ask your doctor about using a peak flow meter. A peak flow meter can tell you when an episode is coming—even before you feel symptoms. Taking medicine before you feel symptoms can stop the episode. People over age 4 with moderate or severe asthma should use a peak flow meter at least daily."

Prior Art: Mechanical Peak Flow Meters

In mechanical peak flow meters, the breath displaces a string-retarded deflector, which moves a pointer along a scale to indicate the test results. Most mechanical meters are simply pieces of molded plastic that have relatively poor inter-device accuracy and reproducibility. In their day these devices were useful to obtain fairly accurate readings, particularly where relative performance was more useful than absolute results. The creation of a longitudinal record depended solely on the discipline and care exercised by the user. Several examples of the mechanical type are listed below.

Prior Art: Electronic Peak Flow Meters and Spirometers

In the earliest models of electronic peak flow meters and personal spirometers, designers merely substituted a pneumotach sensor for the spring-retarded deflector in the mechanical device. All models use a microprocessor to handle the computations and a liquid crystal display to present the numerical test results.

Although current models of portable electronic spirometry devices offer more measurements and good reliability than mechanical peak flow meters, they offer little improvement to the practical challenge of maximizing the utility of home spirometry for both the user and the physician. Their many shortcomings are listed below.

1. They are expensive because their designs are not inherently low cost.
2. They fail to minimize the inconvenience of daily monitoring regimens by not creating a memory-resident longitudinal record which is immediately accessible via the device's human interface.
3. They do not present any trend information by showing the results of preceding tests.
4. They do not deliberately focus the user's attention on airway status and trend; their human interfaces are poorly suited for use by small children.
5. They do not allow the user to label some test results as post medication results.
6. They do not provide the user with a low cost mechanism to deliver the clinical information to the physician in a timely and efficient manner.
7. They do not provide the physician with a crisp, graphical report designed to facilitate a sound, rapid interpretation and good medical treatment decisions.
8. They fail to shield the physician from needing a computer to collect and review data.
9. They do not address physicians' need to track compliance with the management plan nor a systematic method for reviewing the efficacy of the asthma management plan.
10. They do not provide for the systematic collection of test results for statistical analysis.

SUMMARY OF THE INVENTION

One aspect of the present invention is a reporting system that achieves an economical method of collecting, processing, and disseminating clinical data obtained by individuals in the course of practicing their coordinated care plan prepared by their physician to aid in the long-term management of chronic disease. A hands-free, two-way communications link between a physician and patient for use in handling a chronic disease is established.

According to another aspect of the invention, a new "programming" adds new information to the link between physician and patient in a low-cost peripheral that enables collection and dissemination of measured data in a low-cost and efficient manner.

According to another aspect of the present invention a unique monitoring system creates, documents, and reports a chronological record of status information of a physiological characteristic. The only burden on the patient is to take measurements at prescribed times.

According to one aspect of the invention, the monitoring system includes a monitor module for use by the patient, and a remote reporting system. The monitor module includes a processor, a memory, and a time stamp generator and stores low density medical information, comprising data records including the value of a measured characteristic and a time stamp indicating when the characteristic was measured, in the memory. The module includes an interface and a communication protocol for transferring the low density medical information to the report generating system over the communication system.

According to a further aspect of the invention, the reporting system includes a relational data base storing patient records including measured values and time stamps. When data records are downloaded from a remote module the patient record is updated with the latest data records. The transmission of measurement data from the device to the reporting system can cause or trigger the production and transmission of a report to the patient's physician.

According to still further aspect of the invention, a report request is received from a health provider over the communication system for a particular patient and provided to the reporting system. The reporting system accesses the patient record, generates a report showing the chronological record of the measured characteristic in graphical format and transmits the report to the health care professional over the communication system.

According to a still further aspect of the invention, a user interface includes display areas corresponding to zones of respiratory performance. When a respiratory function is measured the zone of performance corresponding to the present measurement is determined and the corresponding display zone is activated.

According to a still further aspect of the invention, a low-cost respiratory function sensor includes a sensor chamber having a cylindrical part and a mouthpiece part. The mouthpiece is oriented to direct air flow tangentially against the outer circular surface of the cylindrical part and the cylindrical part has a rotor mounted therein which rotates when a patient blows into the mouthpiece.

According to a still further aspect of the invention, the rotor has a central section oriented along the axis of rotation and rotor blades extending from the central section to intercept tangential air flow at the circular boundary of cylindrical part. A bar magnet is disposed in the central section and a coil is utilized to generate pulses in response to the changing magnetic field when the rotor spins.

Additional features and advantages of the invention will be apparent in view of the following detailed description and appended drawings.

BRIEF DESCRIPTION OF THE DRAWINGS

FIGS. 4A–4D2 are diagrams depicting the user interface;

DESCRIPTION OF THE PREFERRED EMBODIMENT

Figure 1:
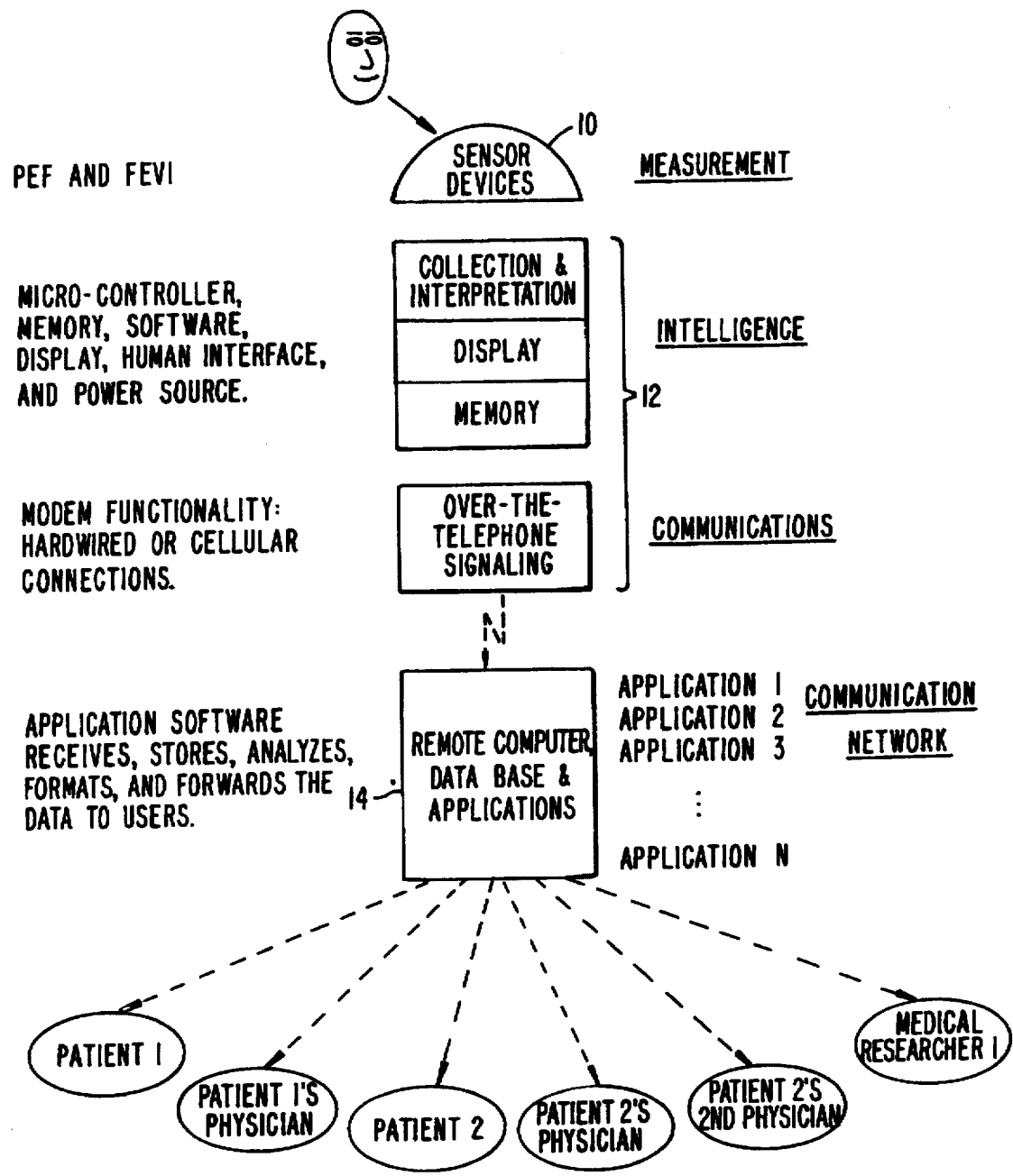
FIG. 1 is a functional block diagram of the measuring, monitoring, and reporting system.

FIG. 1 depicts a functional overview of the measuring, monitoring, and reporting system of the present invention. A sensor device 10 is used to measure the value of a selected physiological characteristic of a patient such as respiratory functions, e.g., peak expiratory flow (PEF) and forced expiratory volume ($FEV_1$), blood glucose levels, blood pressure, heart rate, body weight, fluid intake and discharge rates, and caloric intake. Sensors for measuring these values and providing a digital sensor output encoding the measured values of the physiological characteristics are commercially available. A particular sensor for measuring respiratory functions will be described more fully below.

The intelligence and communications functions are provided in a monitor module 12 which is used by the patient. The sensor may be integrated into the monitor module 12 or be separate with a cable or other means, e.g., an IR beam, used to transfer the digital sensor output to the monitor module 12. The monitor module 12 performs the intelligence functions of collection and interpretation of measured values encoded in the digital sensor outputs, the memory function of storing multiple measured values along with time stamps indicating when measurements were taken, the display function of visually communicating the interpreted measurements to the patient, and the communication function for transferring measured values and time stamps via the telephone system. The intelligence and communication functions may be separated into different modules in other embodiments.

A remote reporting system 14, coupled to the monitor module 12 by the telephone system, performs the functions of receiving the information transmitted from the monitor module 12, of updating a database of longitudinal patient records to add the information transferred from the monitor module 12 to the record of the patient utilizing the monitor module 12, of generating patient reports in graphical formats, and of communicating the reports to physicians or patients. Thus, reports are faxed to the physician to emulate a "medical telegram" and the physician is shielded from needing a computer to collect and review data. Although an initial preferred embodiment will provide delivery by fax, a report of a given patient's data can be delivered to one or more physicians by telephone facsimile, electronic mail, broadcast data communications, or regular mail service. Likewise, the patient can receive a copy of the report by similar means.

Figure 2:
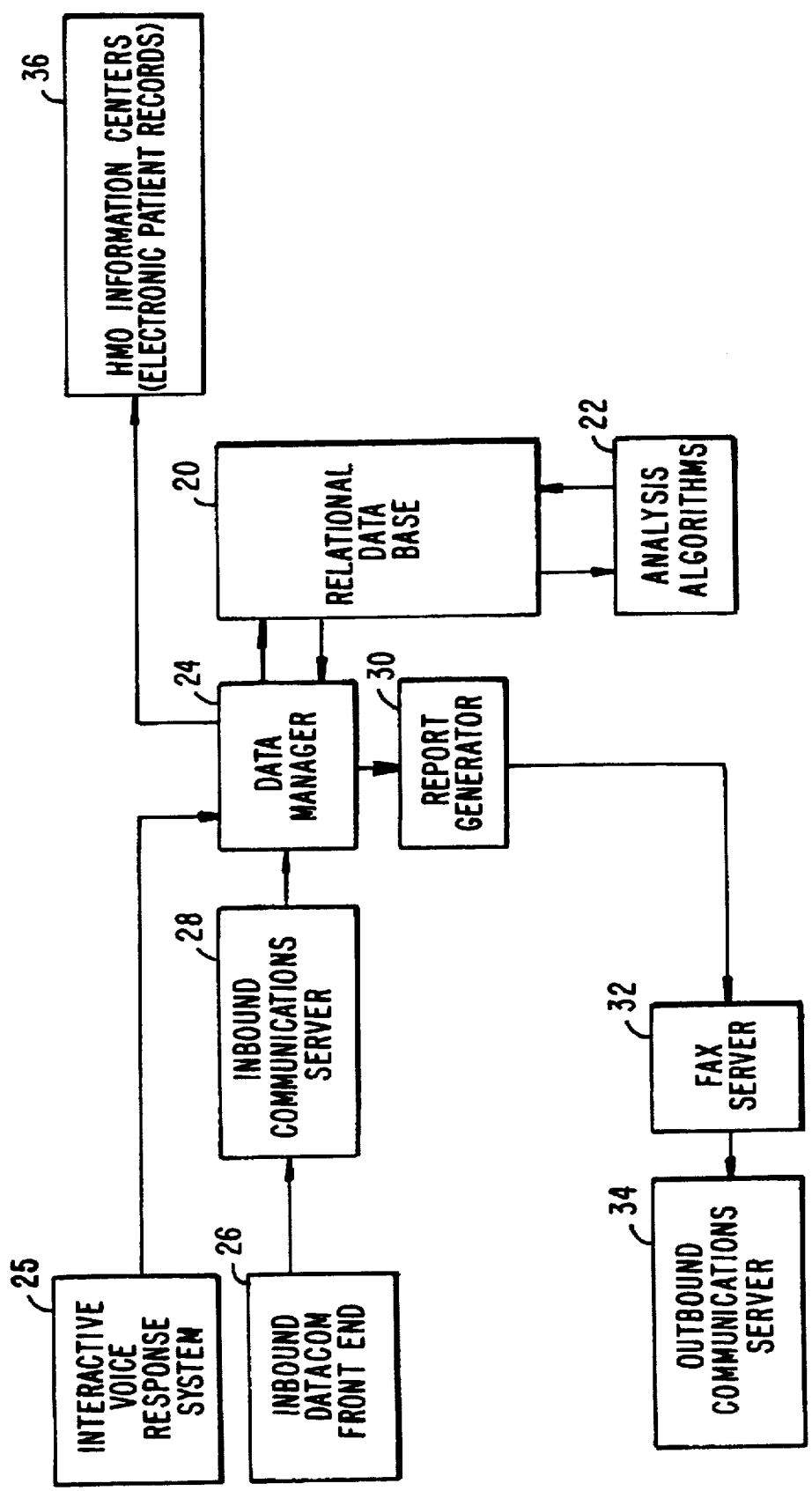
FIG. 2 is a block diagram of the software architecture of the reporting system.

FIG. 2 is a block diagram of the software architecture of the remote reporting system 14. The core of the system of is a relational database 20 for storing longitudinal patient records, including measured values and time stamps provided by the monitor module 12, and analysis algorithms 22 for manipulating the records and data in the database. The longitudinal records include unique ID codes pairing a patient and a remote sensor and a subscription pairing a device ID with a care provider.

A data manager 24 interfaces the data base 20 to various input/output blocks and control blocks such as an Interactive Voice Response System 25. This interactive voice response system allows medical professionals to submit requests for reports based on selections from a menu of report types. Inbound data from a monitor module 12 is received at an Inbound DataCom Front End 26 which interfaces to the telephone system and the data is transferred to the inbound data port of the data manager 24 through an Inbound Communications Server 28.

An outbound data port of the data manager 24 is connected to a report generator 30. The report generator outputs reports via a fax server 32 and Outbound Communications Server 34. Additionally, a second output port transfers electronic patient records to HMO Information Centers 36. Thus, the longitudinal records can be electronically transferred to facilities having computer resources to process the data to generate reports or the reports themselves can be transmitted to individual physicians without requiring the intervention of a computer.

Figure 3:
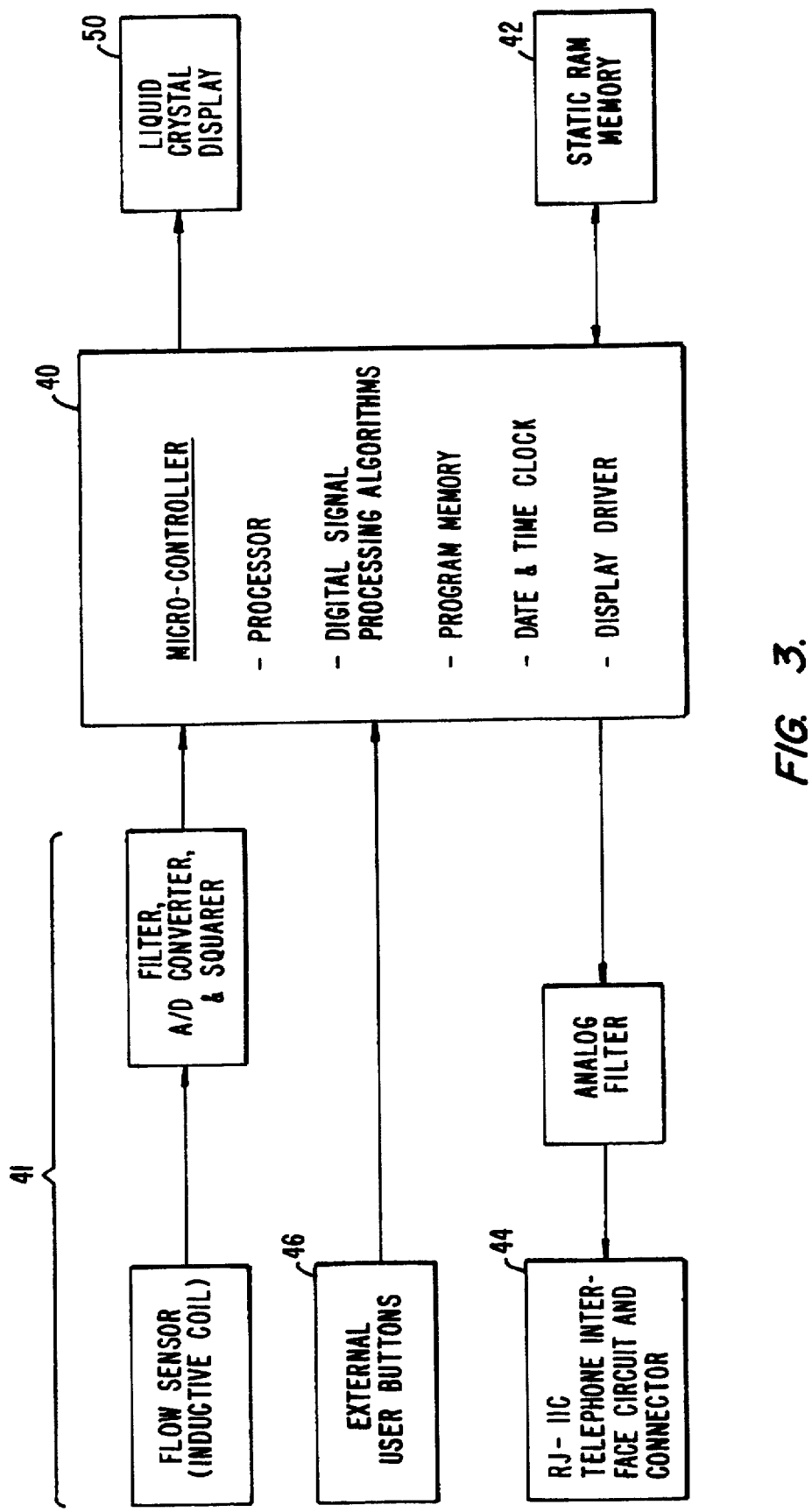
FIG. 3 is a block diagram of the hardware architecture of the monitor.

FIG. 3 is a block diagram of the functionality of the monitor module 12. The monitor module 12 is controlled by a single-chip micro-controller 40, such as a Motorola MC 6805, that includes on-chip memory for storing application programs and other data. The micro-controller 40 interfaces with the other functional blocks utilizing standard data, address, and control buses which are not part of the invention. The interconnection of the micro-controller 40 and functional blocks is depicted schematically in the figure. As depicted, the micro-controller includes on-board digital signal processing algorithms, program memory, a date and time clock, and a display driver.

The micro-controller 40 receives sensor output digital data 41 when a patient measures the value of a physiological characteristic and forms a data record encoding the value of the measured characteristic, a time stamp indicating the time and date when the measurement is taken, and unique ID code, which is the serial number of the individual device stored within its internal circuitry, identifying the monitor module 12. Data records are stored in a RAM 42 as a circular file. The internal file structure of a "data record" has its own specialized, embedded instruction set that identifies several data types, including measurement values, time and date, personal best value, and zone boundary values. If the RAM 42 is full then a most recent data record will be written over the oldest data record.

The micro-controller 40 also responds to the user tagging a single test with a visual marker in the display. The tag is inserted as an extra element into a data record in the device memory. The physician can instruct the patient to mark individual test results as "post-medication" tests according to certain rules. When the tag is used in this manner, i.e., as a post-medication marker, the reporting system can provide reports that show the patient's response to medication (e.g., the response to a bronchodilator).

The micro-controller is also programmed to implement a set-up procedure allowing the user to choose between two settings for the session length, 0 and 10. When the session length is set to 0, the device stores the result of every measurement into its long-term memory. When the session length is set to 10, the device stores the best PEF and FEV1 values achieved in a ten minute interval, which begins with the first blow in a potential series of blows. The session lengths are varied so that the general use of the device could conform with currently accepted practice of performing up to three blows in a test session and documenting only the best result of the three. Thus, the device provides for performing the Peak Expiratory Flow test in accordance with guidance published by the National Asthma Education Program and the American Thoracic Society.

A telephone interface 44 is controlled by the micro-controller to transfer records from the RAM 42 to the remote reporting system 14.

When the patient wishes to down-load data records from the monitor module 12 the patient connects a telephone line to an RJ-11C telephone jack in the telephone interface 44 and simply pushes a button on the user interface. The micro-controller then executes an application program to retrieve data records from the RAM 42, convert the digital data to analog signals, and control the telephone interface circuit to connect the remote reporting system 14 and to transfer the retrieved data records to the remote reporting system 14.

In the preferred embodiment, a modem chip is not used to transfer data in order to avoid the extra cost of including another chip. Instead, the micro-controller 40 executes custom application software to drive specialized circuitry to perform a binary file transfer to the remote computer at 300 Baud according to the Bell 103 standard. Error detection is achieved by using the cyclic redundancy checking during the binary file transfer. In other embodiments the file transfer scheme may be implemented to use a faster data rate (e.g., 1200 Baud) and a different Bell standard (e.g., bell 201 or 212).

FIGS. 4A-4C depict a special user interface 50, controlled by micro-controller 40, that presents the result of a measurement of respiratory functions in terms of peak flow zones.

To help patients manage their asthma, the Expert Panel Report published by the NIH presents the system of peak flow zones. In the zone model each test result is expressed as a percent of one's Personal Best, defined as the highest peak flow level that the user normally achieves when his or her airway is clear. The zones are analogous to traffic light signals—i.e. green, yellow and red—to make it easier to remember. Each zone identifies a percentage of the Personal Best. The Green Zone is 80%–100% of the Personal Best; the Yellow Zone is 50%–80%; and the Red Zone is less than 50% The personal best and boundaries between the zones are configurable values that can be adjusted by the patient. Any adjustments should be made with the specific approval of the physician.

The display 50 has three rows 52, 54, and 56 of rectangular display areas formed thereon. The bottom row 52 of display areas is red, to correspond to the red zone, the middle row 54 of display areas is yellow, to correspond to the yellow zone, and the top row 56 of display areas is green, to correspond to the green zone.

In a preferred embodiment, the zone chart consists of a five row by nine column array of dots. The green zone 56 and yellow zone 54 each have two rows of dots on the zone chart portion of the display 50. The two rows bisect the zones to provide better resolution. Thus, if the green zone 56 covers 80 to 100% of the personal best, the lower corresponds to 80 to 90% and the upper row to 90 to 100%. Similarly, if the yellow zone 54 covers 50 to 80% of the personal best, the lower corresponds to 50 to 65% and the upper row to 65 to 80%.

The micro-controller 40 selectively activates the display areas of the display 50. A personal best data record is stored in the RAM 42 along with zone defining values. When the micro-controller 40 receives a digital sensor output it executes an application program to retrieve the personal best data record and zone defining values from the RAM 42 and to determine which zone includes the value encoded in the received digital sensor output.

The micro-controller 40 then activates the farthest right display area of the row of display area corresponding to the zone that includes the measured value. Thus, the user is immediately informed whether the measured value is in the red, yellow, or green zone and does not need any familiarity or understanding of numerical values.

Other characteristics of the display are illustrated in FIGS. 4A-4D2. For example, display areas to the left of the rightmost display area in each row display the zone including previously measured values. Thus, the patient can see whether his performance is improving or deteriorating over time. Additionally, an animated character's (the Welby character) arm is moved when the present measured value switches zones to highlight the change of the zone to the patient. Numeric displays may also be activated. The micro-controller 40 includes application programs responsive to the user input to activate the various display areas of the display 50.

The human interface of the monitor was designed to facilitate use by children and adults. It has several important facets:

only three buttons for simplicity of operation;

its display device (an LCD) employs multiple functional areas listed below;

a number line for reporting measurement results and calculated values, a zone chart for reporting zone status using position-and-color coded dots, an animated character, "Welby", whose actions and expressions reinforce the meaning of the reported airway status information, and various symbols which annotate items of information presented on other parts of the display (e.g., units of measurement such as Liters/minute, Liters, AM, PM, the personal best crown, the red zone cross, the telephone) or which convey specific messages (e.g., the low battery indicator).

When the results of a measurement are reported to the patient on the device's display, the information is presented in several ways concurrently. The presentation of information in each functional area of the display is designed to maximize the probability that the user will comprehend the meaning of the display and will remember or know how to look up the appropriate action to take given the patient's current airway status.

Another unique aspect of the display format is breaking up the presentation of results from a single test into separate frames to avoid making the display too complicated or busy and thus rendering it less effective. The device presents the complete data for each blow in a sequence of two or more frames on the display, depending on which elements of data are desired. The standard review uses two frames which present different data elements on the number line: 1) the peak flow in liter/minute and percent of personal best; and 2) the date and time of measurement. Each frame also included the activated zone chart, the Welby character, and various symbols. The optional review, which is activated by pressing the center button, adds a third frame which included the FEV1 in liters.

As depicted in FIG. 4D, the various configurations of the Welby character are used in the written coordinated care program that a physician typically prepares for a patient. A given configuration of the Welby character is used as a label adjacent to the description of the therapy prescribed for instances in which the patient's airway status is within a given zone.

Figure 5B:
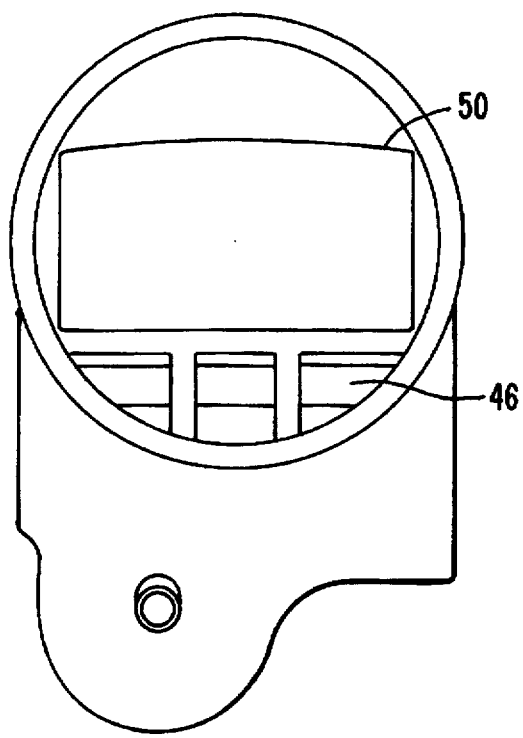
FIGS. 5A, 5B, and 5C are views of the monitor housing.
Figure 5A:
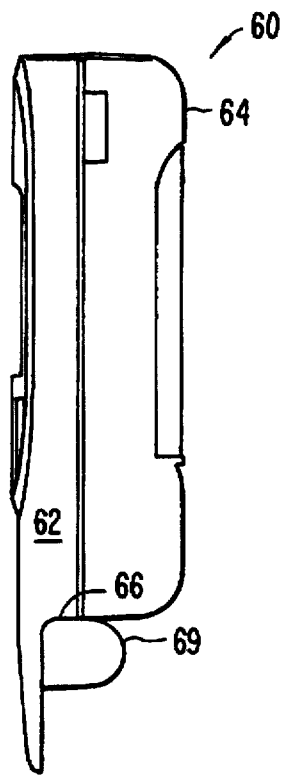
Figure 5C:
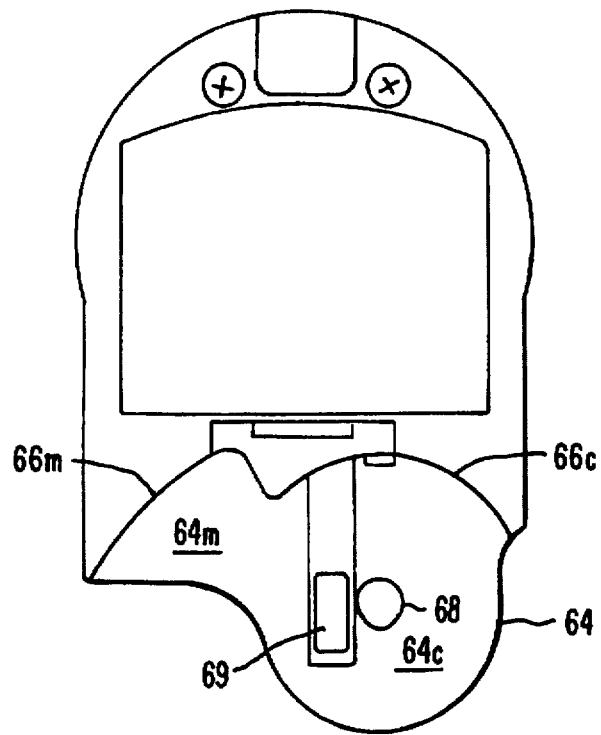

A preferred embodiment of a sensor/monitor module assembly will now be described with reference to FIGS. 5A–5C, 6A–6B, 7A–7B, and 8. As will be apparent from the following description, the monitor/module is a stand-alone device useful to asthma patients for monitoring their condition. Referring to FIG. 5A, a monitor housing 60 includes top and bottom plates 62 and 64. FIGS. 5B and 5C are front and back views, respectively, of the top plate 62. The front surface has the LCD display 50 and user input buttons 46 disposed thereon. Turning to FIG. 5C, a projection 64 at the bottom part of the top plate 62 includes a circular part 64c and a mouthpiece storing part 64m. The projection is bordered by a projection edge 66 having an arc-shaped portion 66c and a mouthpiece abutting portion 66m. Additionally, a mounting post 68 is disposed at the center of the circular part 64c of the projection 64 and a coil housing 69 is disposed on the circular part 64c displaced slightly from the center.

Figure 6A:
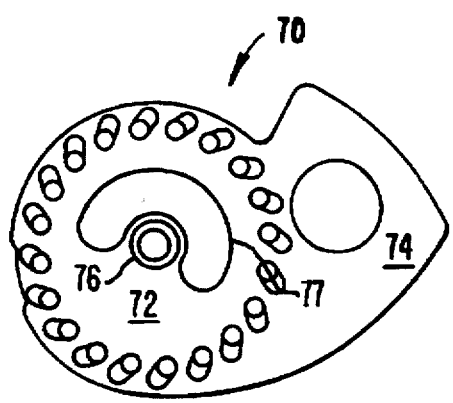
FIGS. 6A and 6B are views of the sensor chamber.
Figure 6B:
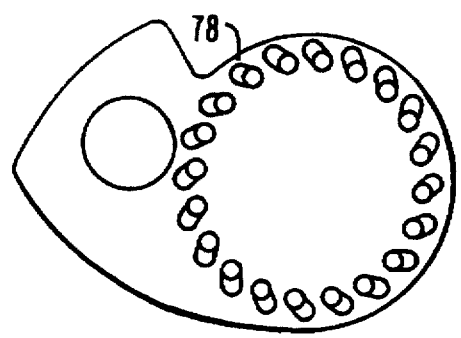

FIGS. 6A and 6B are top and bottom views of a sensor chamber 70. Referring to FIG. 6A, the chamber 70 includes a cylindrical chamber part 72 and a mouthpiece part 74. The cylindrical chamber part 72 has a circular cross-section with an axial connector 76 formed at the center of the top surface of the cylindrical section and an arc-shaped coil housing aperture 77, centered at the axial connector 76 and displaced radially therefrom, formed in the top surface of the cylindrical chamber part 74. Sets of vent holes are formed in the top and bottom surfaces of the cylindrical chamber part 74 and are disposed along a circular path centered disposed near the outer circumference of the cylindrical chamber part 74.

Figure 7A:
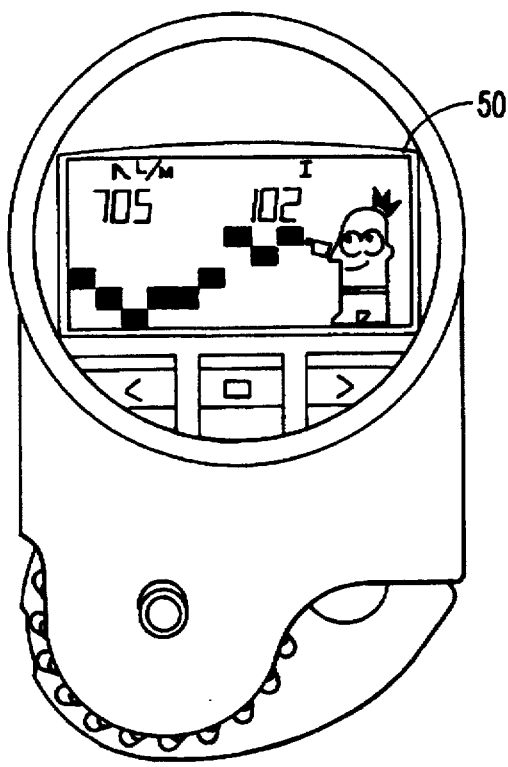
FIGS. 7A and 7B are views of the assembly.
Figure 7B:
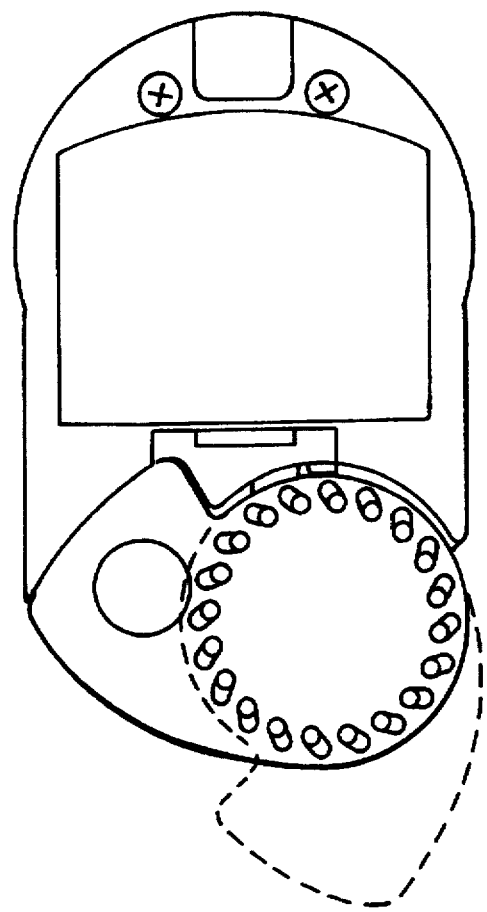

FIGS. 7A–7B depict the monitor module/sensor assembly with the sensor housing 70 in the closed position. The mounting post 68 on the projection 66 is registered with the axial connector 76 so that the sensor chamber 70 rotates about the mounting post from a closed position (shown) to an open position (phantom). In the closed position the opening of the mouthpiece part 74 abuts the mouthpiece abutting section 66m of the projection edge 66 to seal off the mouthpiece. In the open position the patient seals his lips about the opening of the mouthpiece and blows into the chamber to measure air flow. The mouthpiece rotates between the open and closed positions to help keep out lint and debris.

Figure 8:
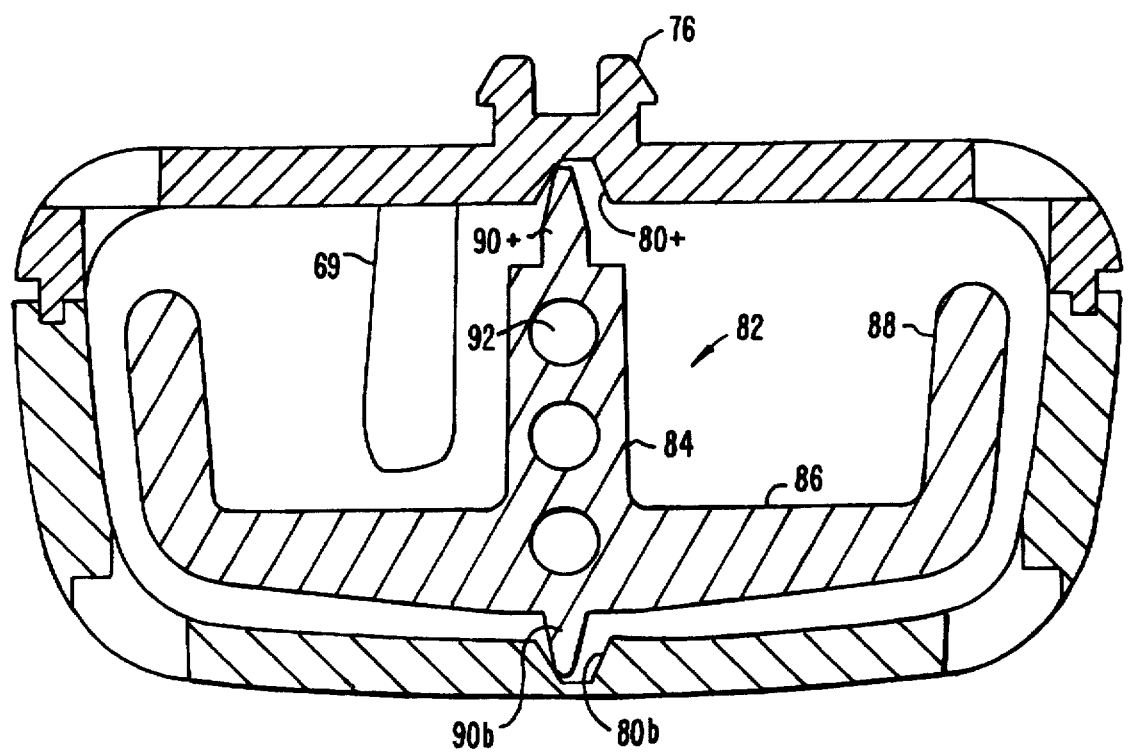
FIG. 8 is a cross-sectional view of the sensor chamber.

The operation of the sensor to measure PEF and FEV$_1$ will now be described with reference to FIGS. 8 and 9. FIG. 8 is a cross-sectional view of the cylindrical chamber part 72. The bottom and top interior surfaces have bearing receptor cups 80t and 80b formed therein. A rotor 82 includes a central post 84 with rotor blades 86 extending therefrom. The rotor blades 86 include vertical vanes 88 disposed near the cylindrical side surface of the cylindrical section 72. Pointed bearings 90t and 90b are formed on the top and bottom of the central post 84 and register with the bearing receptor notches 80t and 80b. The central post 82 includes at least one bar magnet 92 shown in cross-section in the Figure.

The rotor within the sensor includes two sub-assemblies: the four-bladed rotor 82 and the cylindrical magnet 92, which fits permanently into the rotor's shaft so that the long axis of the magnet is perpendicular to the rotor's axis of rotation. The tips 88 of the rotor's shaft fit loosely into small cups 80t and 80b in the interior surface of the top and bottom sub-assemblies of the sensor. There are no bearings involved in this junction; the tips of the rotor's shaft rest in these small cups.

When a patient blows into the sensor chamber, the rotor spins like a top, with the tips of its shaft turning within the cups. In the event that sputum or mucus gets lodged in or around these pivot points, the loose fit of the tip of the rotor shaft into the cups allows for easy cleaning under a stream of tap water.

When a patient blows into the mouthpiece opening of the sensor housing 70 the air flow is directed against the cylindrical side wall of the chamber 70 and impinges on blades 88 to cause rotation of the rotor. About 30 milliliters of air pass through the chamber 70 for each rotation of the rotor. The air exits through the vent holes 78 to prevent the build-up of back pressure. The sensor chamber 72 is mechanically designed to achieve a vortical flow when the patient blows into it. Furthermore, note that the four-bladed rotor spins around its maximum principal moment of inertia, just like a top, thereby eliminating the potential for bearing chatter and drag.

Figure 9:
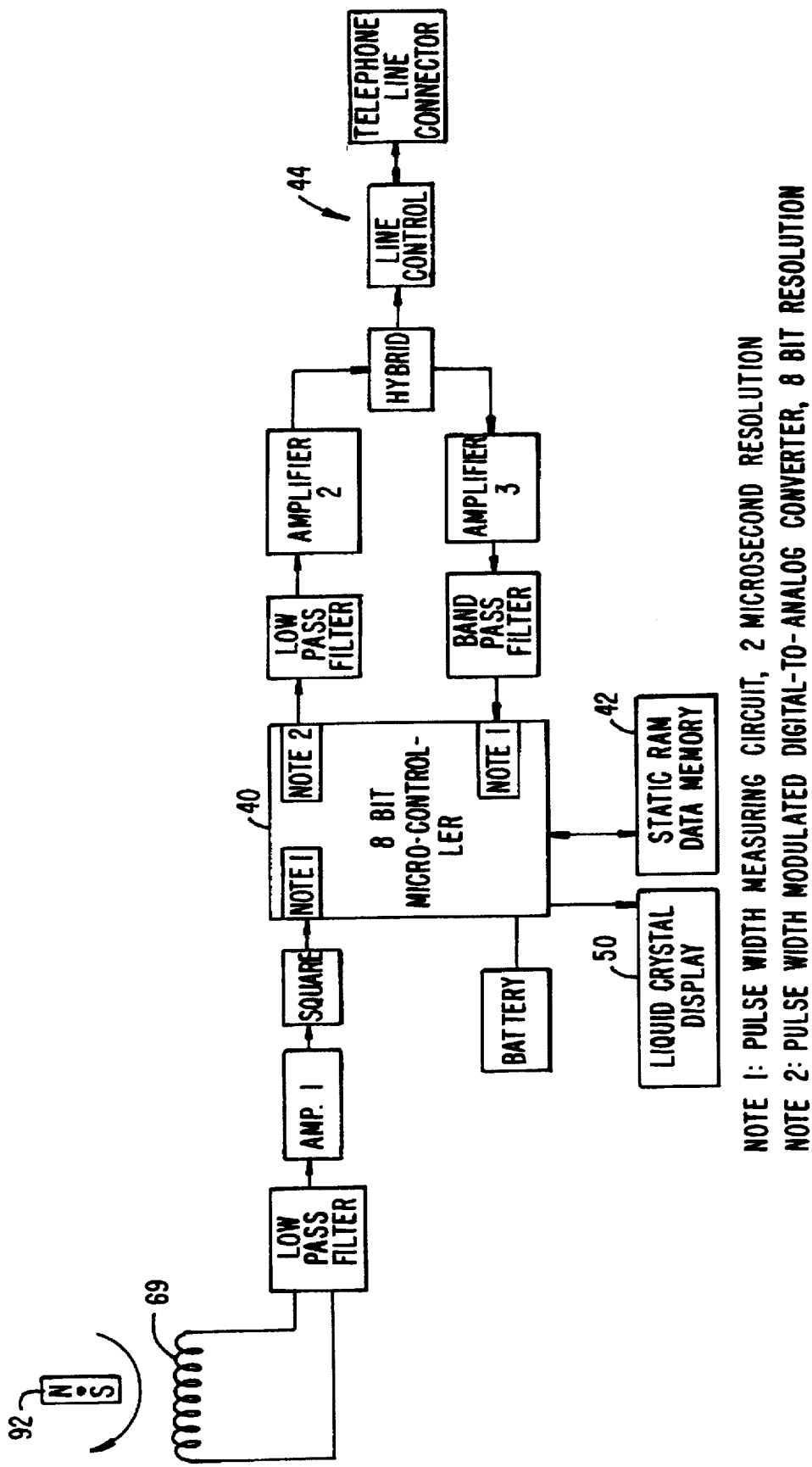
FIG. 9 is a block diagram of the respiratory flow measuring system.
Figure 10A:
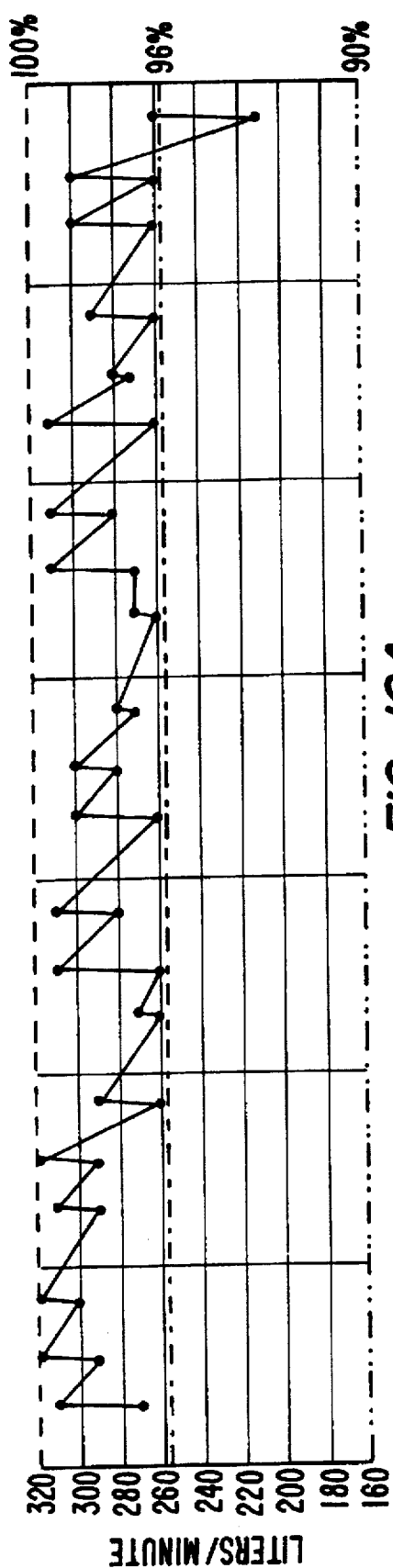
FIGS. 10A–10J are graphs depicting chronological records of respiratory function.
Figure 10B:
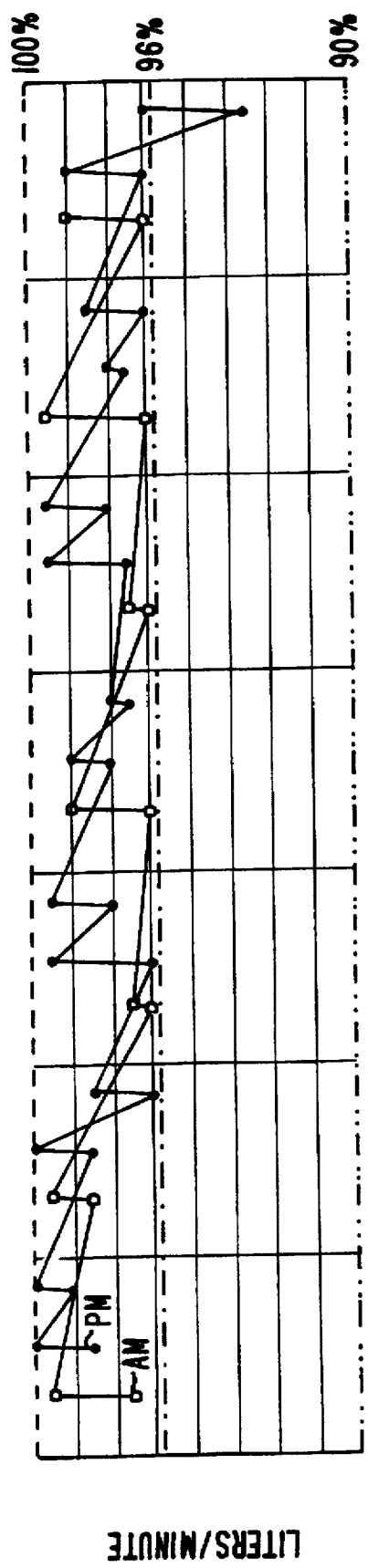
Figure 10C:
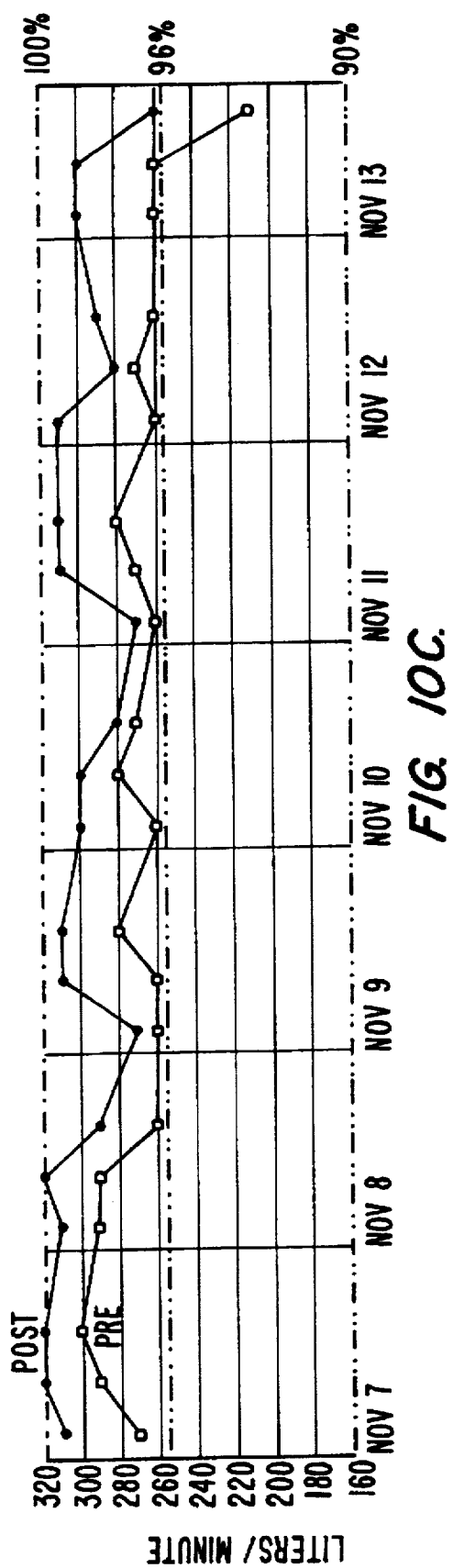
Figure 10D:
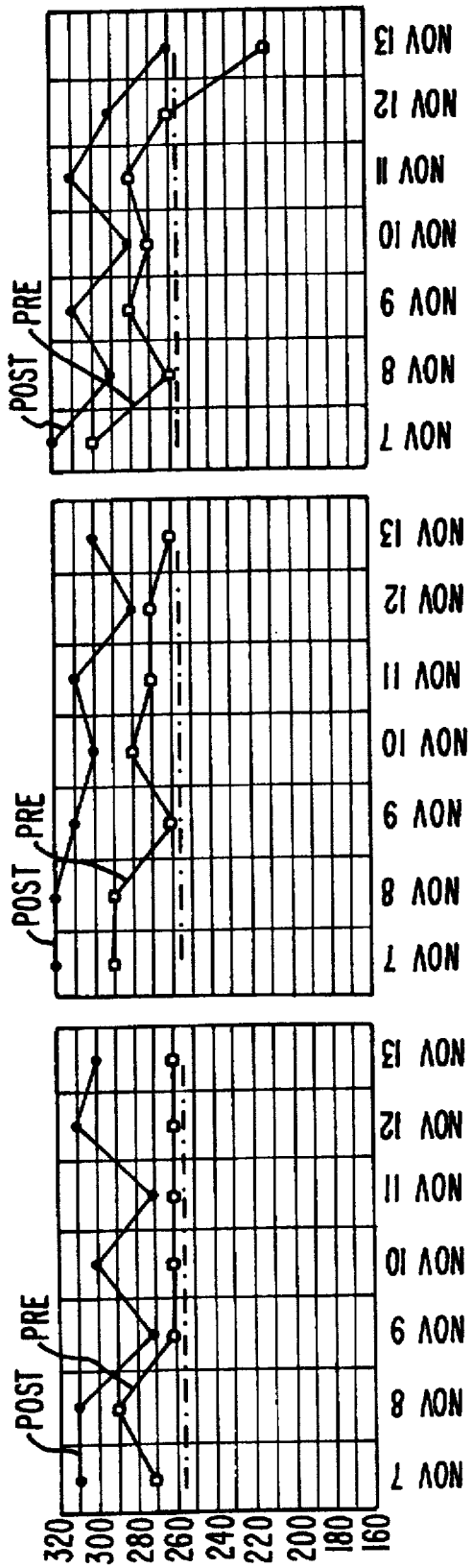
Figure 10E:
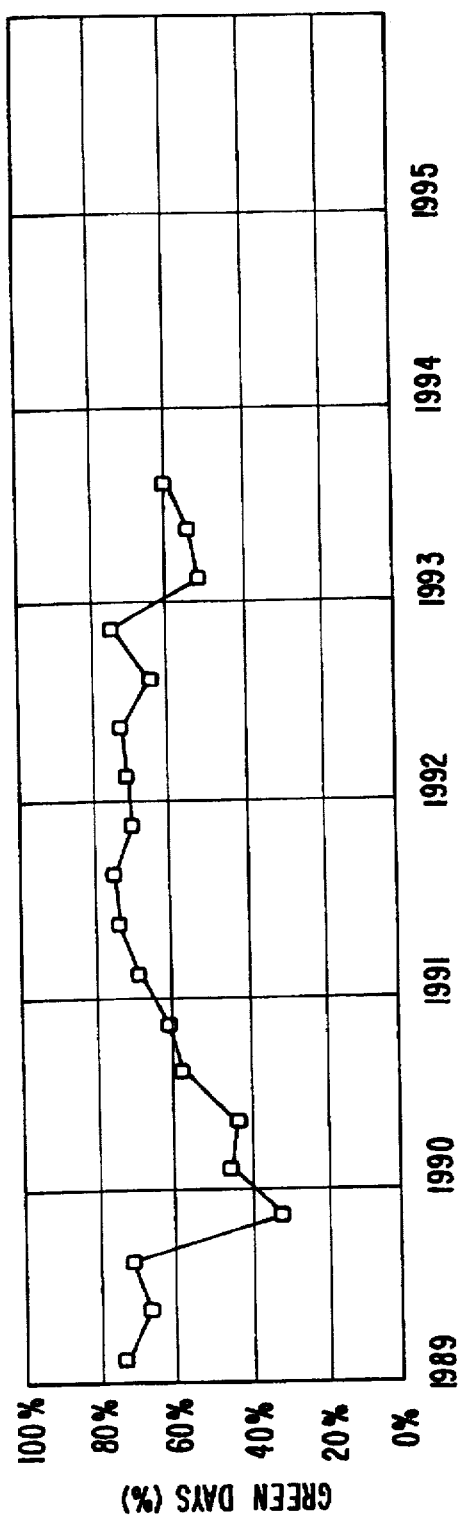
Figure 10F:
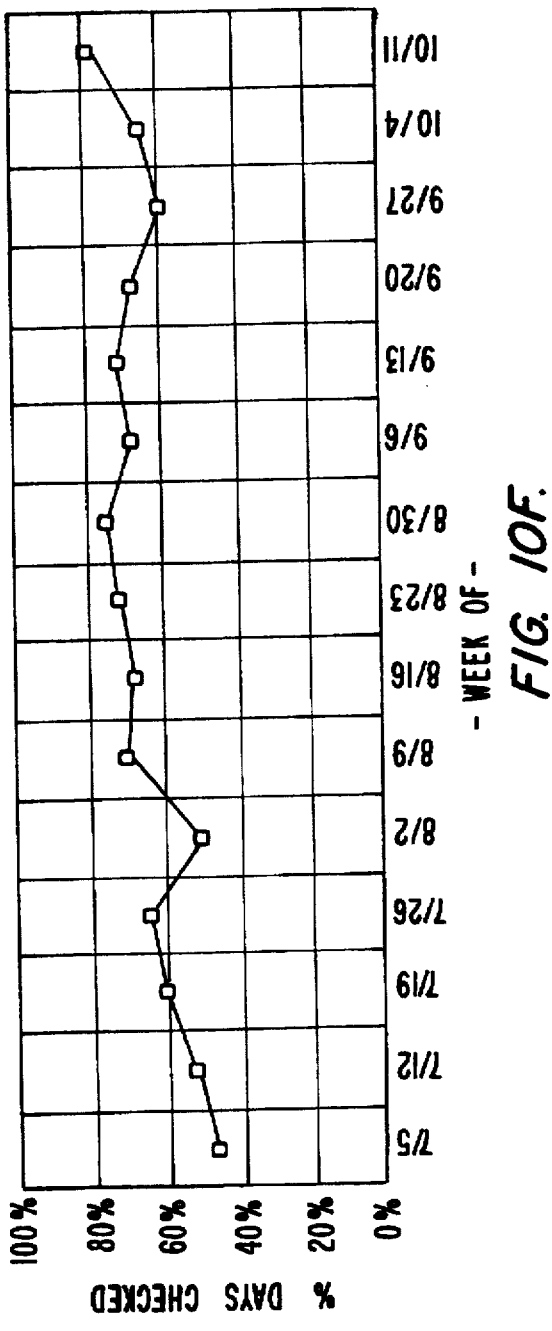
Figure 10G:
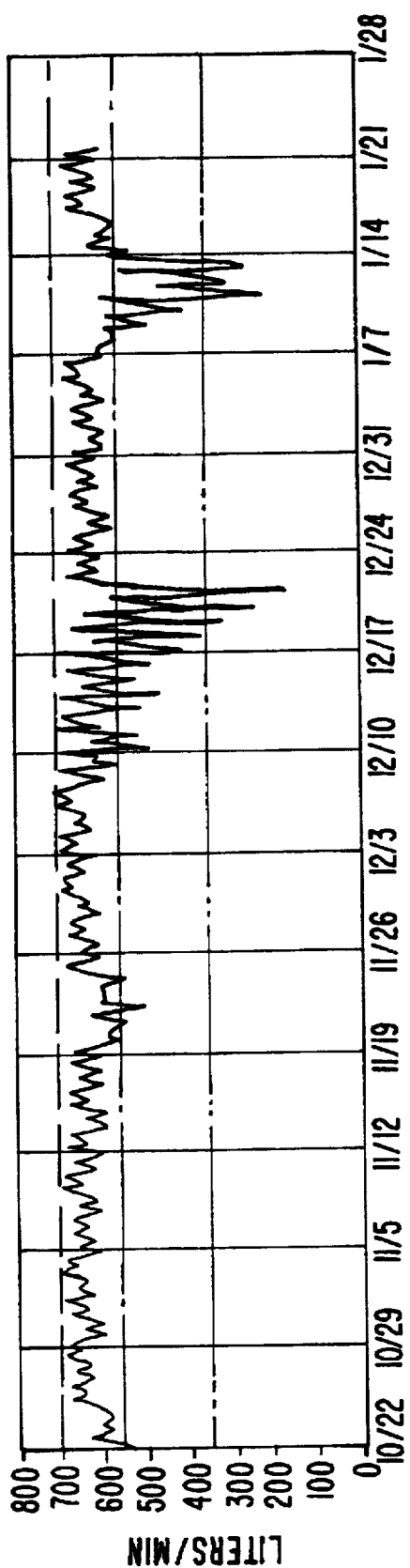
Figure 10H:
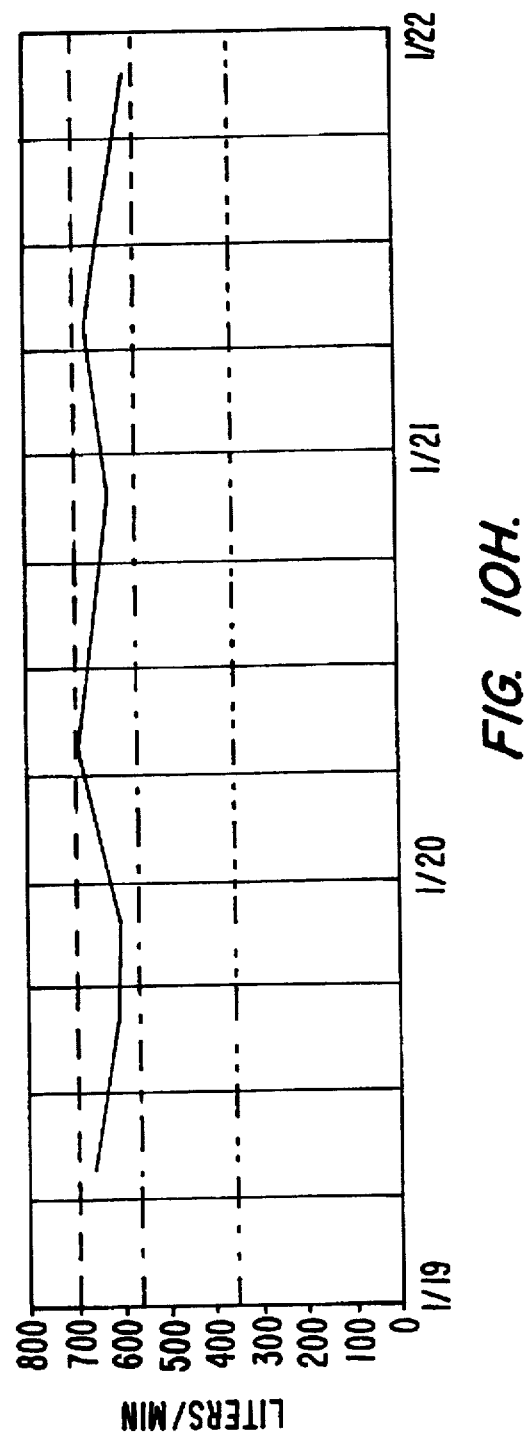
Figure 10I:
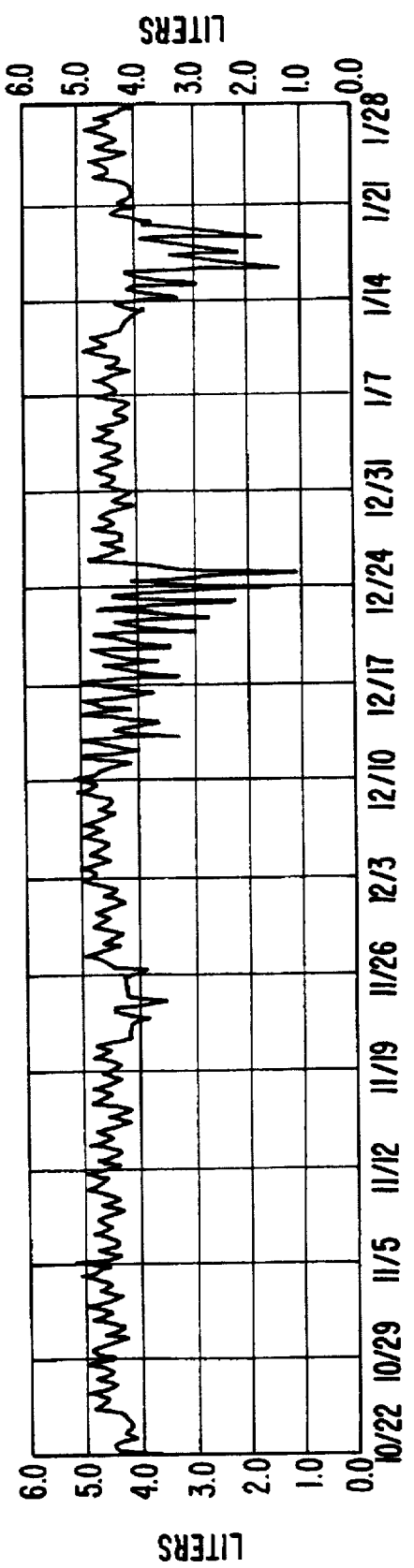
Figure 10J:
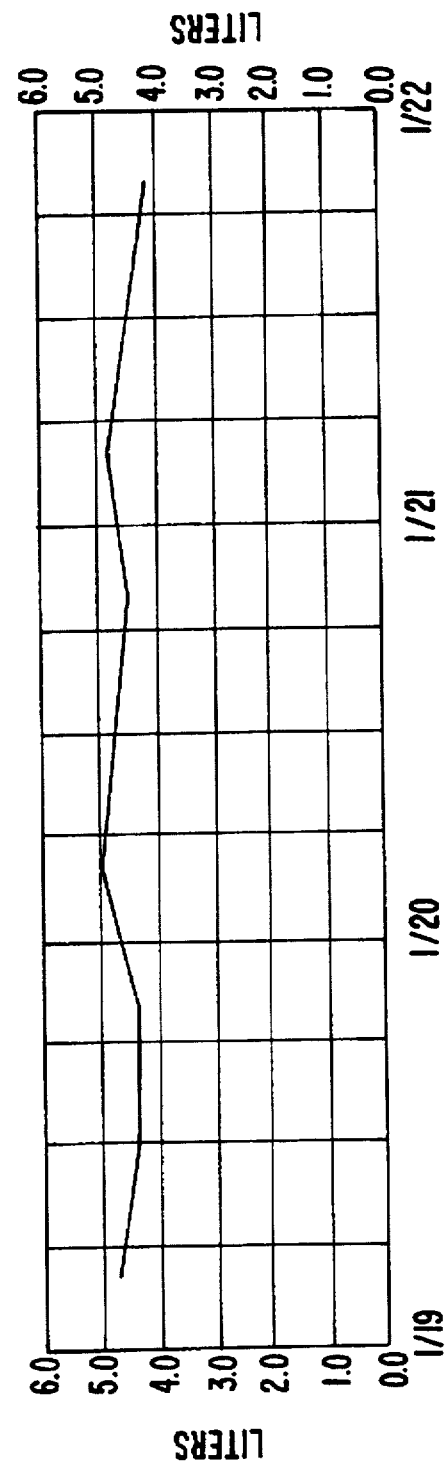

FIG. 9 is a particular implementation of the generalized system depicted in FIG. 3 for utilizing the sensor depicted in FIG. 8. In FIG. 9, the coil 69 generates two pulses each time the bar magnet 92 completes a rotation. The pulses are amplified and filtered to produce digital transitions. The time between each transition is processed by the microcontroller 40 executing application software. The PEF and FEV$_1$ are calculated and stored in the RAM 42 as a part of a data record.

From FIG. 8 is seen that the rotation bearing is a "sloppy bearing" not requiring a high precision fit. Thus, all parts of the sensor can be manufactured of plastic utilizing low-cost processes. Additionally, the molding process produces consistent parts, thereby assuring very high device-to-device reproducibility and permitting different sensor chambers (mouthpieces) to be used with any given monitor housing. Moreover, in-the-field calibration of a mouthpiece is not required.

The "sloppy bearing" results in small timing errors from one pulse to the next. Measurements are made on the basis of several pulses so that such effects are averaged out. Additionally, the microcontroller executes a digital compensation program to eliminate the effect of the non-zero moment of inertia. The program is based on several parameters which are matched to the actual rotational dynamics and aerodynamics of the rotor and chamber.

The rotor 80 has a top-like rotation characteristic when rotated about the central post and a non-zero moment of inertia. The micro-controller executes a compensation program to eliminate the effect of the non-zero moment and to calculate the actual value of the PEF and FEV. The program is based on the physical principles involved in calculating the motion of the rotor and includes several parameters which are matched to the actual rotation of the rotor.

FIG. 10 depicts several exemplary graphical formats for reporting respiratory function trends to a physician. These formats illustrate how the simple actions of periodically blowing into the mouthpiece of the sensor and downloading the data to the remote reporting system results in charts showing the respiratory performance of the patient.

Thus, a system for coordinated management of chronic diseases or long-lasting conditions, such as asthma or other lung disease, diabetes, hypertension, and obesity is described. The sensor and monitor interact to eliminate the errors inherent in the current manual process of measuring (misreading error); documenting (incorrect transcription, incomplete transcription); and reporting (omission error) a chronological record of physiological status information. Additionally, the system fosters compliance with a physiological status monitoring program agreed upon by both the patient and physician as component of an overall self-management program for chronic disease or other long lasting conditions. Compliance information can serve as the basis for incentive programs targeted at both patients and physicians. These incentive programs could help motivate patients to comply with the monitoring program and to learn about how to maintain control over the chronic condition. They could also help motivate physicians to work at helping their patients maintain control over the chronic condition. Improvement in compliance is usually achieved by making improvements that render a monitoring tool more convenient, easier to use, and more understandable.

The invention has been described with reference to the preferred embodiments. Alternatives and substitutions will now be apparent to persons of ordinary skill in the art. The dial protocol from the device can be either tone or pulse. Other approaches to the design of the sensor could include multi-pole magnets, multiple coils, smaller or larger sensor chambers (depending on the measurement of interest), optical interrupters and other magnetic sensors (e.g., Hall effect switch, Reed relay and magneto-resistive). When the device transfers a copy of its measurement data record to a remote computer the device may dial the telephone number of the remote computer. The dialing activity may be configured to be compatible with older rotary type of telephone service (pulse) or with contemporary touch-tone type of telephone (tone) Additionally, the link between the monitor and remote computer could be configured either as a wired link, e.g., cable and connectors, a base station in which the monitor rests making electrical contacts, or a wireless link, e.g., radio, infra-red, or acoustic. Accordingly, it is not intended to limit the invention except as provided by the appended claims.

What is claimed is:

1. A system for interfacing a health monitoring sensor, with the health monitoring system of a type for providing a serial digital output signal that transmits a file encoding a measured value of a parameter indicating a measured status of a physiological characteristic of a patient and a time stamp indicating when the measured value was determined, to a remote computer via a telecommunication network, with the remote computer managing a central data base, said system comprising:

a user input device for generating control signals;

a data memory for storing data;

a sensor side interface for receiving a file from said health monitoring sensor;

a patient-side telecommunication interface for transmitting and receiving data from the telecommunication network;

an interface ID unit for storing an ID code uniquely identifying a particular remote interface device;

a micro-controller, responsive to application programs and other data stored in said data memory, and coupled to said sensor side interface to receive a file, including a measured value data element and a time stamp indicating when a measurement is taken, transmitted from said health monitoring sensor, and with said micro-controller coupled to said data memory, said interface ID unit, and said patient-side telecommunication interface, said micro-controller for formatting and compressing said file received from said health monitoring sensor, including said unique ID code, to form a digital transmit file and for embedding a digital instruction set in said digital transmit file identifying several data types including measured values and the time and data stamp, for storing the transmit file in said data memory, and said micro-controller for initiating a data transfer protocol to read one or a plurality of digital transmit files from the memory, convert the digital transmit files to analog signals, establish a connection with the remote computer over said telecommunication network, and transmit said analog signals to said remote computer to transfer transmit files from said memory to said remote computer via the telecommunication network.

2. The system of claim 1 further comprising:

a status indicator for indicating when a data transfer is in progress, when a data transfer has been successfully completed, and when a data transfer has been unsuccessful.

3. A method for interfacing a health monitoring sensor to a remote computer via an interface module coupled to a telecommunication network, with the health monitoring sensor of a type having an sensor output port for providing a digital output signal for transmitting a measurement file encoding a measured value of a parameter indicating the measured status of a physiological characteristic of a patient and a time stamp indicating when a measurement was taken, with the measured value encoded in a first digital format, and with the interface module having a data input port adapted to be coupled the sensor output port, a data memory, a programmable microcomputer, and telecommunication port adapted to be coupled to said telecommunication network, and with the remote computer managing a central data base for storing patient records, with the interface module performing said method which comprises the stems of:

receiving the measurement file from said health monitoring sensor, with the measurement file including a first measured value and a time stamp;

generating a unique ID code;

creating a digital transmit file in said memory when the measurement file is received from said health monitoring sensor, with said digital transmit file including the measured value, said time stamp, and said unique ID code:

embedding a digital instruction set in said digital transmit file identifying several data types including measured values and the time and data stamp;

writing said digital transmit file to said memory;

transferring one or a plurality of digital transmit files to said central database in response to a command from a user interface, said step of transferring further comprising the steps of:

reading one or a plurality of digital transmit files from the memory;

converting the digital transmit files to analog signals;

establishing a connection with the remote computer over said telecommunication network; and transmitting said analog signals to said remote computer to transfer measurement files from said memory to said remote computer via the telecommunication network.

4. The method of claim 3 further comprising the steps of:

indicating when a data transfer from the memory to the remote computer is in progress, has been successfully completed, or has been unsuccessful.

5. The method of claim 3 further comprising the step of:

ordering the digital transmit files in the memory in time sequence as indicated by time stamps included in the records to form a diary of when measurements are taken by a patient.

* * * * *